(12) United States Patent
Lampropoulos et al.

(10) Patent No.: US 10,065,017 B2
(45) Date of Patent: Sep. 4, 2018

(54) CATHETER WITH CATHETER TIP AND RELATED METHODS

(71) Applicant: Merit Medical Systems, Inc., South Jordan, UT (US)

(72) Inventors: Fred Lampropoulos, Salt Lake City, UT (US); Nicholas Gerald Accisano, Howell, NJ (US)

(73) Assignee: Merit Medical Systems, inc., South Jordan, UT (US)

( * ) Notice: Subject to any disclaimer, the term of this patent is extended or adjusted under 35 U.S.C. 154(b) by 605 days.

(21) Appl. No.: 14/674,143

(22) Filed: Mar. 31, 2015

(65) Prior Publication Data

US 2015/0283357 A1 Oct. 8, 2015

Related U.S. Application Data

(60) Provisional application No. 61/989,289, filed on May 6, 2014, provisional application No. 61/974,012, filed on Apr. 2, 2014.

(51) Int. Cl.
*A61M 25/00* (2006.01)
*B32B 37/00* (2006.01)
*B32B 37/12* (2006.01)
*B32B 37/18* (2006.01)

(52) U.S. Cl.
CPC ...... *A61M 25/0069* (2013.01); *A61M 25/001* (2013.01); *A61M 25/008* (2013.01); *B32B 37/0038* (2013.01); *B32B 37/12* (2013.01); *B32B 37/182* (2013.01); *A61M 25/0026* (2013.01); *A61M 25/0032* (2013.01); *A61M 2025/0004* (2013.01);

(Continued)

(58) Field of Classification Search
CPC ...... A61M 25/0069; A61M 2025/0004; A61M 25/008; A61M 2025/0081; A61M 25/0026; A61M 25/0032; A61M 2025/0035

See application file for complete search history.

(56) References Cited

U.S. PATENT DOCUMENTS 4,747,840 A * 5/1988 Ladika ............... A61M 25/0041
604/264
4,921,483 A * 5/1990 Wijay ............... A61M 25/1002
604/102.02

(Continued)

OTHER PUBLICATIONS

International Preliminary Report dated Oct. 13, 2016 for PCT/US2015/023604.

(Continued)

*Primary Examiner* — Nathan R Price
*Assistant Examiner* — Courtney Fredrickson
(74) *Attorney, Agent, or Firm* — Stoel Rives LLP (57) ABSTRACT

An elongate catheter tip may be coupled to an elongate catheter body adjacent a distal end of the catheter body. To couple a catheter tip to a catheter body, a proximal portion of the catheter tip may (1) be disposed between a first elongate member and an second elongate member and (2) be subsequently fused to the second elongate member and the first elongate member. The resulting catheter and catheter tip may, among other functions, facilitate the measurement of differences in fluid pressure and/or facilitate the delivery of fluid or medical devices during a medical procedure.

18 Claims, 9 Drawing Sheets

(52) U.S. Cl.
CPC ............... *A61M 2025/0035* (2013.01); *A61M 2025/0081* (2013.01); *B32B 2535/00* (2013.01); *Y10T 156/10* (2015.01)

(56) References Cited

U.S. PATENT DOCUMENTS

| | | | |
|---|---|---|---|
| 5,364,344 A * | 11/1994 | Beattie | A61M 25/003 604/43 |
| 5,419,777 A | 5/1995 | Hofling | |
| 6,368,301 B1 | 4/2002 | Hamilton et al. | |
| 8,613,706 B2 | 12/2013 | Langston | |
| 2002/0052641 A1 | 5/2002 | Monroe et al. | |
| 2002/0107506 A1* | 8/2002 | McGuckin, Jr. | A61M 1/285 604/523 |
| 2005/0115624 A1* | 6/2005 | Walak | A61M 25/0009 138/139 |
| 2005/0154439 A1 | 7/2005 | Gunderson | |
| 2006/0009740 A1* | 1/2006 | Higgins | A61M 25/001 604/264 |
| 2012/0089070 A1 | 4/2012 | Moehle et al. | |

OTHER PUBLICATIONS

International Search Report and Written Opinion dated Jun. 22, 2015 for PCT/US2015/023604.

\* cited by examiner

CATHETER WITH CATHETER TIP AND RELATED METHODS

RELATED APPLICATIONS

This application claims priority to U.S. Provisional Application No. 61/974,012, filed on Apr. 2, 2014 and titled, "Cather with Catheter Tip and Related Methods," and U.S. Provisional Application No. 61/989,289, filed on May 6, 2014 and titled, "Cather with Catheter Tip and Related Methods," both of which are hereby incorporated by reference in their entireties.

TECHNICAL FIELD

This application generally relates to medical devices, components of medical devices, and methods of making and/or using such devices and/or components. More particularly, in some embodiments, this application relates to catheters comprising a catheter tip that is coupled to a catheter body.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

This application generally relates to medical devices, components of medical devices, and methods of making and/or using such devices and/or components. More particularly, this application relates to medical devices, such as catheters, that are configured to be at least partially disposed within a body lumen or lumens during a medical procedure. For example, in some embodiments, a catheter comprises a catheter tip that is coupled to a catheter body. The catheter tip may be coupled to the catheter body by fusing the catheter tip to a first elongate member and a second elongate member of a catheter body. Such devices may be used, inter alia, to monitor fluid pressure, to detect and/or determine differences in fluid pressure, and/or facilitate the delivery of fluids and/or devices during a medical procedure.

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is used in its ordinary sense, and is broad enough to refer to any suitable coupling or other form of interaction between two or more entities, including mechanical, fluid, and thermal interaction. Two components may interact with each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other. A lumen is in "primary fluid communication" with fluid at a particular region of a patient's body if fluid at that region may enter into the lumen without traversing a valve.

The directional terms "proximal" and "distal" are used herein to refer to opposite locations on a component or device. The proximal end of a component or device is defined as the end of the device closest to the practitioner when the device is in normal use by the practitioner. The distal end is the end opposite the proximal end, along the longitudinal direction of the device, or the end farthest from the practitioner during normal use.

Two components may be "coaxial" even if the components adopt a non-linear conformation. For example, a second tube may be coaxially disposed within a first tube that adopts a non-linear conformation if the second cylindrical tube remains centrally disposed within the first cylindrical tube.

Medical devices, such as catheters and components used with catheters, may be employed during medical procedures to access locations within a patient's body. In some embodiments, the catheter may be configured to deliver fluid or other materials to locations within a patient's body. Additionally or alternatively, the catheter may be configured to measure fluid pressure in one or more lumens.

For example, in some embodiments, a catheter comprises one or more side ports or other openings that are configured to allow body fluid from a first region of a patient's body to enter into a first lumen of the catheter. The catheter may also comprise one or more side ports or other openings that are configured to allow body fluid to enter into a second lumen from a second region that is distinct from the first region. The first and second lumens may be configured to be coupled to one or more sensors (e.g., pressure sensor(s), pH sensor(s), or temperature sensor(s)) that detect and/or measure the fluid pressure or facilitate the determination of other characteristics of fluid disposed within the lumens (e.g., pH, temperature). In some embodiments, the sensor may be incorporated within the catheter, delivered through a catheter lumen, and/or disposed adjacent a proximal end of a catheter lumen. A catheter with a first lumen and a second lumen that are in primary fluid communication with fluid from different regions of a patient's body may facilitate the determination of differences in blood pressure or other characteristics at the two regions.

For example, a catheter may be configured to detect and/or measure differences in blood pressure across an obstruction or valve. In an exemplary embodiment, a multi-lumen catheter comprising multiple ports and/or other openings may be inserted into a patient such that a first lumen is in primary fluid communication with fluid on one side of the valve and a second lumen is in primary fluid communication with fluid on the other side of the valve. By coupling each lumen to one or more pressure sensors, the difference in blood pressure across a valve may be determined. Measuring the difference in blood pressure across a valve may be particularly important in connection with procedures relating to the function of heart valves, such as valvuloplasty. For example, during a valvuloplasty procedure (or other medical procedure), differences in blood pressure across a valve may be determined by placing a first lumen in primary fluid communication with fluid in a ventricle on one side of a valve (e.g., a semilunar valve) and a second lumen in primary fluid communication with fluid in the aorta.

A multi-lumen catheter may alternatively or additionally be configured to measure the flow rate of a fluid within a lumen. For example, a cold fluid may be delivered through a first lumen of a catheter to an upstream location within a patient while a thermister or other temperature sensor may be delivered through a second lumen or otherwise disposed at downstream location. By measuring the change in temperature over a period of time subsequent to delivery of the cold fluid, the flow rate of the fluid may be estimated or determined.

A multi-lumen catheter may alternatively or additionally be configured to monitor or deliver an electrical pulse. For example, a first electrode may be delivered through a first lumen of a catheter to a first location within a patient and a second electrode may be delivered to a second location within a patient. Disposed in this manner, the electrodes may be used to monitor or deliver one or more electrical pulses. More particularly, electrodes disposed in this manner may be used to monitor electrical pulses across a heart or to function as a defibrillator or pacemaker by delivering one or more electrical pulses to the heart.

Some multi-lumen catheters may additionally or alternatively be used both to deliver fluids and/or solids through a first lumen and to detect and/or measure fluid pressure or other fluid characteristics through a second lumen. For example, a catheter may comprise a first lumen that is configured to deliver medicaments, contrast agents, medical devices and/or other materials and a second lumen that is configured to detect and/or measure fluid pressure (e.g., blood pressure). In some embodiments, delivery through a first lumen and fluid pressure detection or measurement through a second lumen may occur simultaneously. In some embodiments, the flow rate and/or pressure of fluid delivered through the first lumen may be controlled and/or monitored to ensure proper delivery of the fluid.

Figure 1:
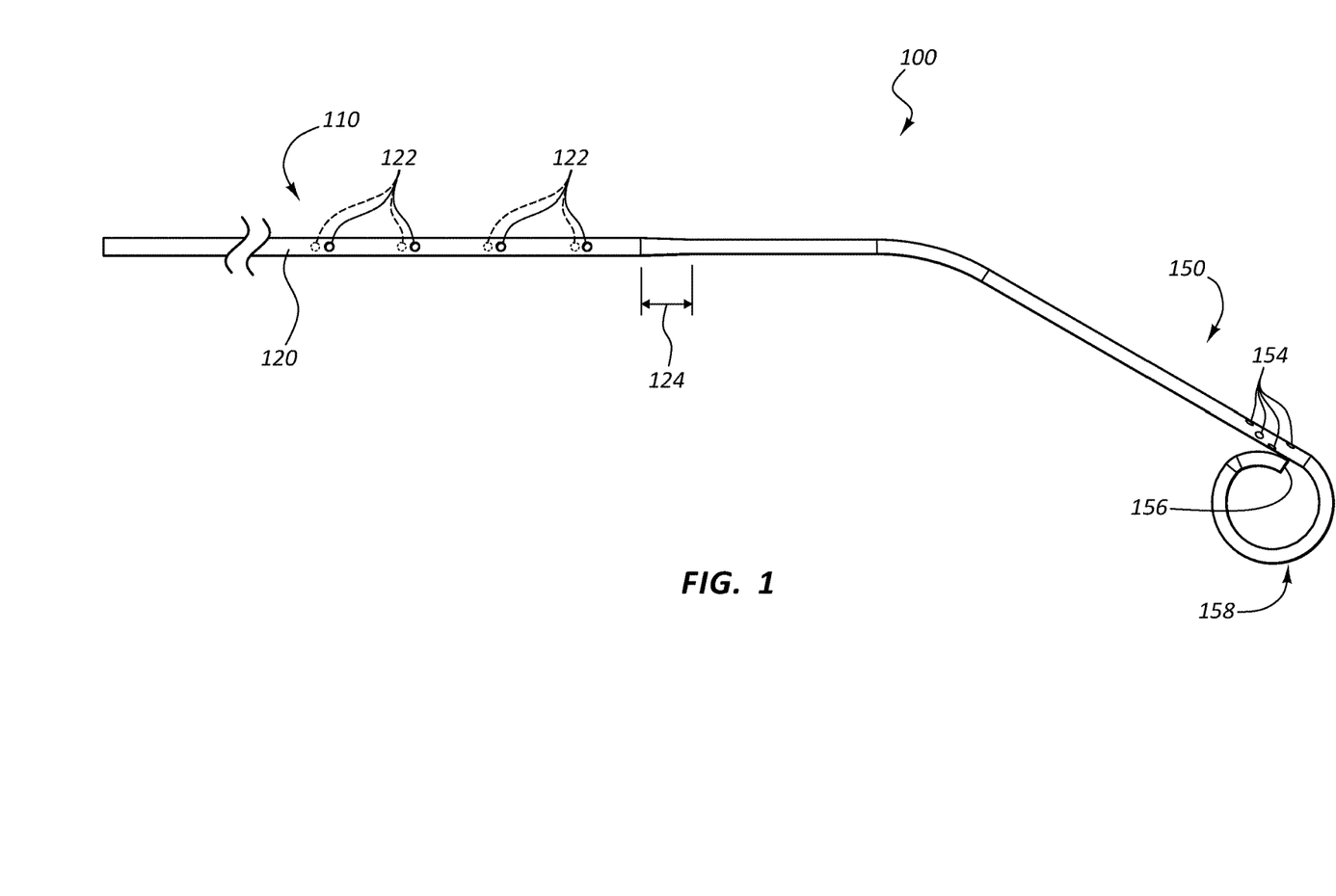
FIG. 1 is a side view of a catheter in an assembled state.

FIG. 1 provides a side view of a catheter 100 in an assembled state. The catheter 100 may comprise an elongate catheter body 110 and an elongate catheter tip 150 that is coupled to the elongate catheter body 110. The catheter tip 150 may comprise a distal opening 156 and/or one or more side ports 154 that are in fluid communication with a first lumen that extends through the catheter tip 150. The catheter tip 150 may also comprise a curved distal region 158 that is configured to facilitate atraumatic advancement of the catheter tip 150 within a lumen (e.g., blood vessel) of a patient. For example, the curved distal region 158 of the catheter tip 150 may adopt a rounded (e.g., pigtail) conformation such that, as the catheter 100 is advanced within the lumen of the patient, body lumen surfaces are initially contacted by a curved surface rather than the blunt distal end 156 of the catheter 100.

The catheter tip 150 may be coupled to the elongate catheter body 110 adjacent the distal end of the elongate catheter body 110. The elongate catheter body 110 may comprise a first elongate member 120 with one or more side ports 122 that are configured to allow fluid to enter into one or more lumens. The one or more lumens may be distinct from the first (e.g., central) lumen that extends through the catheter tip 150. These one or more lumens may be configured to facilitate the measurement of fluid pressure.

In some embodiments, the first elongate member comprises a diameter of 5-7 French and the catheter tip comprises a diameter of 4-6 French. The catheter body 110 may additionally or alternatively comprise a tapered region 124. The tapered region 124 may comprise a portion of the first elongate member 120 and/or a portion of the catheter tip 150. In the embodiment depicted in FIG. 1, the tapered region 124 comprises a distal end and a proximal end. The distal end of the tapered region may have a smaller outer diameter than the proximal end of the tapered region 124. For example, in some embodiments, the tapered region may taper from an outer diameter of 0.075-0.100 inches at the proximal end to an outer diameter of 0.06-0.07 inches at the distal end. In some embodiments, the tapered region tapers from a diameter of 5-7 French to a diameter of 4-6 French. For example, the tapered region may taper from a diameter of 6 French to a diameter of 5 French. In some embodiments, the tapered region may continuously taper over a length of 0.250-0.500 inches.

In some embodiments, the catheter tip 150 comprises an elastomer that renders the catheter tip 150 "softer" and/or more flexible than the elongate catheter body. A relatively soft and/or flexible catheter tip may, alone or in combination with a curved distal region 158, facilitate atraumatic advancement of the catheter 100 through a body lumen and/or facilitate traversal of a curved path. In some embodiments, the catheter tip 150 has a hardness of 30-60 Shore A.

The elongate catheter body 120 may comprise a set of material properties that differs from the material properties of the elongate catheter tip 150. For example, the elongate catheter body 110 may be harder and/or stiffer than the catheter tip 150. In some embodiments, the elongate catheter body 110 has a hardness of 60-70 Shore D. The elongate catheter body 110 may be configured to provide pushability through a body lumen and sufficient torque transference to enable rotation of distal regions of the catheter 100 by manipulation that occurs adjacent the proximal end of the catheter body 110. In some embodiments, the elongate catheter body 110 is configured to provide more torque transference per unit of length than the elongate catheter tip 150. The elongate catheter body 110 may also comprise a structural support element, for example to increase the torque transference of the elongate catheter body 110.

Figure 2A:
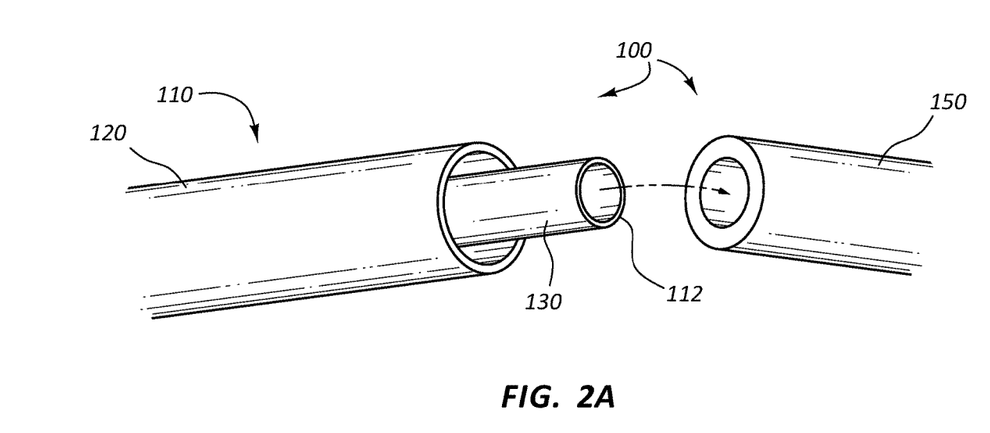
FIG. 2A is a perspective view of a portion of the catheter of FIG. 1 in a disassembled state.
Figure 3:
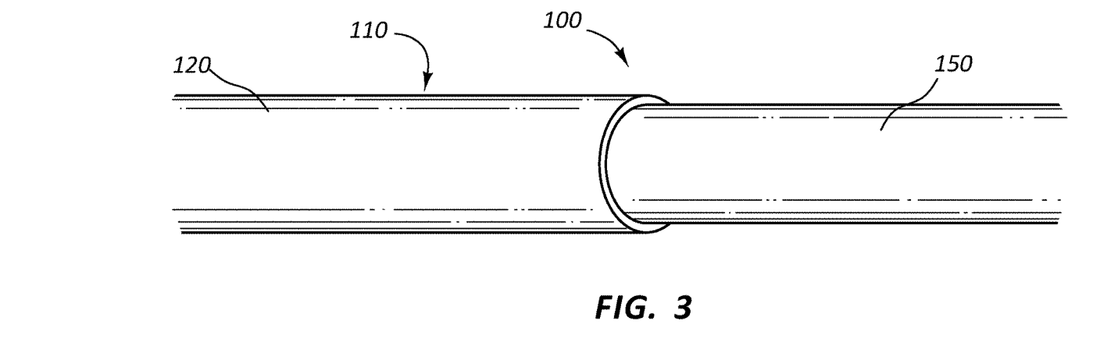
FIG. 3 is a perspective view of a portion of the assembled catheter of FIG. 1.

FIGS. 2A and 3 provide perspective views of a portion of the catheter 100 in a disassembled state and an assembled state. In the disassembled state shown in FIG. 2A, the catheter tip 150 is not coupled to the elongate catheter body 110. In the assembled state shown in FIG. 3, the catheter tip 150 is coupled to the elongate catheter body 110. With reference to FIGS. 2A and 3, the elongate catheter body 110 may comprise a first elongate member 120, a second elongate member 130, septal walls (not shown), and a distal end 112. The second elongate member 130 may be at least partially disposed within the first elongate member 120.

The first elongate member 120 may be a generally cylindrical and tubular structure. In some embodiments, the first elongate member 120 comprises an elastomer, such as polyether block amides (e.g., PEBAX).

The second elongate member 130 may be a generally cylindrical and tubular structure. The second elongate member 130 may be disposed within the first elongate member 120 such that the second elongate member 130 is coaxial to the first elongate member 120. The second elongate member 130 may alternatively or additionally comprise a distal portion that extends beyond a distal end of the first elongate member 120. More particularly, in some embodiments, the distal portion of the second elongate member 130 extends beyond the distal end of the first elongate member 120 a distance of 0-10 mm.

Figure 2B:
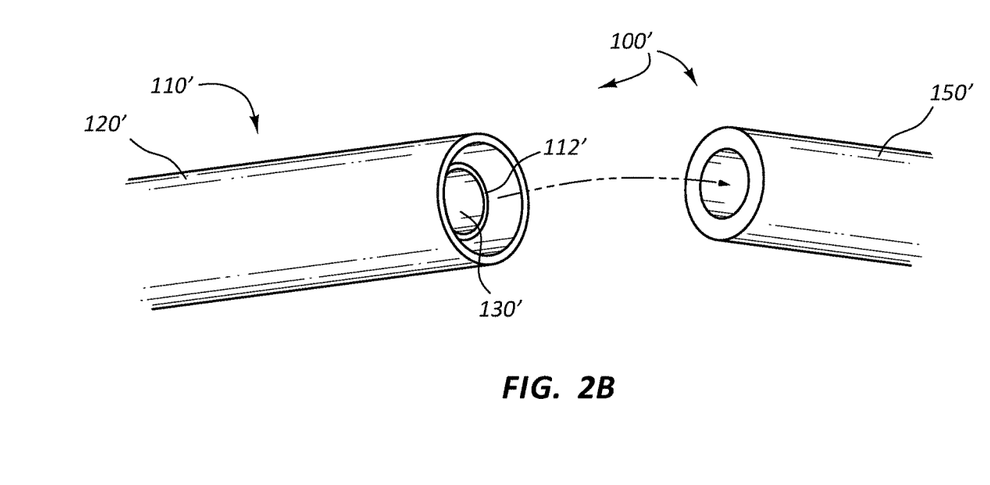
FIG. 2B is a perspective view of a portion of a catheter in a disassembled state.

In other embodiments, such as the embodiment shown in FIG. 2B, the catheter 100' comprises a first elongate member 120' that extends distally further than the second elongate member 130'. In other words, the distal end 112' of the second elongate member 130' may be disposed proximal of the distal end of the first elongate member 120'. More particularly, in some embodiments, the distal end of the first elongate member 120' extends 0-10 mm, 1-5 mm, and/or 1-2 mm beyond the distal end 112' of the second elongate member 130'. Extension of the first elongate member 120' distally with respect to the second elongate member 130' may change the stress distribution and/or bending characteristics of portions of catheter 100' disposed adjacent the distal end of the elongate catheter body 110' as compared to the embodiment shown in FIG. 2A. For example, bending or kinking of the catheter may cause stress to concentrate at or adjacent to one or more transition regions of the catheter (i.e., regions where the cross-sectional profile of the catheter changes). For example, along the length of the catheter, the cross-sectional profile of the catheter may transition between any two or more of the following profiles: (1) a profile that includes only the first elongate member and the second elongate member, (2) a profile that includes the first elongate member, the second elongate member, and the distal tip, (3) a profile that includes the first elongate member and the distal tip, (4) a profile that includes the second elongate member and the distal tip; and (5) a profile that includes only the distal tip. Thus, the strain profile of the catheter may be adjusted by altering whether the second elongate member extends beyond the distal tip of the first elongate member and/or by varying the spacing between transition regions.

With reference to FIGS. 2A and 3, the second elongate member 130 may comprise an elastomer, such as polyether block amides (e.g., PEBAX). In some embodiments, the second elongate member 130 comprises a liner or other material to increase the hardness, stiffness, pressure capacity, and/or durability of the second elongate member 130. For example, the second elongate member 130 may comprise steel braids and/or a layer comprising polyimide. More particularly, in some embodiments, the second elongate member 130 comprises an elongate PEBAX tube with a polyimide liner disposed on the inner diameter of the PEBAX tube.

The catheter tip 150 may comprise a proximal portion that is configured to be coupled adjacent the distal end 112 of the elongate catheter body 110 by disposing the proximal portion of the catheter tip 150 between the first elongate member 120 and the second elongate member 130 and subsequently fusing the proximal portion to both the first elongate member 120 and the second elongate member 130. In this manner, the proximal portion of the catheter tip 150 may be disposed around a portion of the second elongate member 130 and disposed within a distal portion of the first elongate member 120. In some embodiments, the proximal portion of the catheter tip has a length of 1-7 mm. In some embodiments in which the second elongate member 130 comprises a distal portion that extends beyond the distal end of the first elongate member 120, disposing the proximal portion of the catheter tip 150 between the first elongate member 120 and the second elongate member 130 may dispose the distal portion of the second elongate member 130 adjacent the inner diameter of catheter tip 150. With the distal portion of the second elongate member 130 adjacent the inner diameter of the catheter tip 150, the distal portion of the second elongate member 130 may be fused to the elongate catheter tip 150. When the catheter tip 150 is coupled to the elongate catheter body 110, a first lumen 160 (see FIG. 4) may extend through both the second elongate member 130 and the elongate catheter tip 150.

Figure 4:
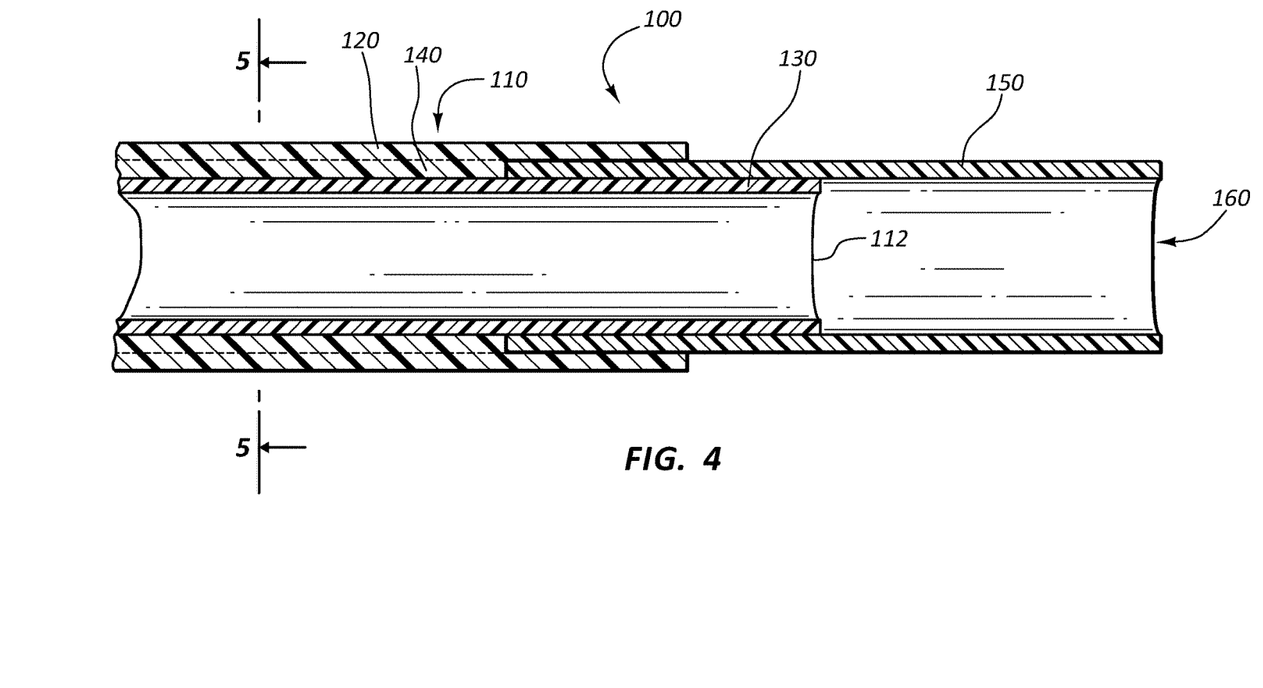
FIG. 4 is a cross-sectional side view of a portion of the assembled catheter of FIG. 1.
Figure 5:
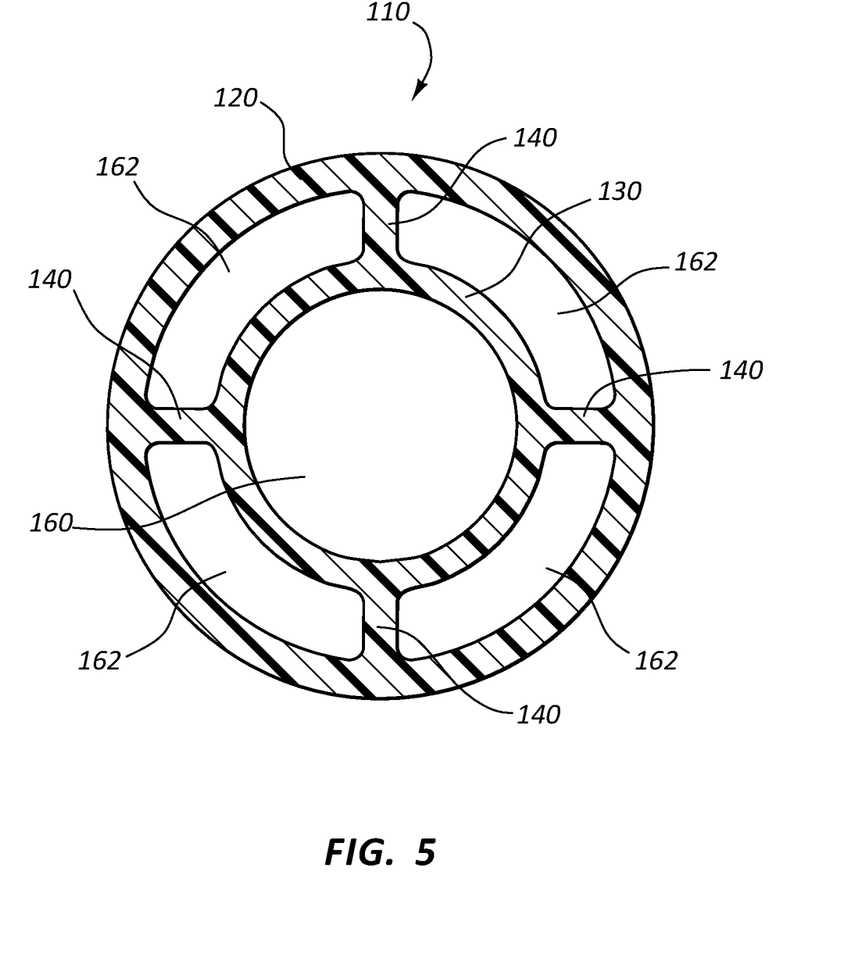
FIG. 5 is a cross-sectional view of the catheter of FIG. 1 taken through line 5-5 of FIG. 4.

FIG. 4 provides a cross-sectional side view of a portion of the assembled catheter of FIG. 1. This figure is intended to schematically illustrate both the structure of a portion of a catheter and methods that may be used to couple a catheter tip to a catheter body. The particular structure, shape, or arrangement of components depicted in this figure is not meant to limit the scope of this disclosure. FIG. 5 provides a cross-sectional view of the elongate catheter body 110 of the catheter 100 taken through line 5-5 of FIG. 4.

The portion of the catheter depicted in FIG. 4 shows a catheter tip 150 with a proximal portion disposed between the first elongate member 120 and the second elongate member 130 of an elongate catheter body 110. The catheter tip 150 may be generally tubular in shape and configured to couple to the elongate catheter body 110. The catheter 100 may comprise a first lumen 160 (see FIG. 5), such as a central lumen, that extends through both the second elongate member 130 and the catheter tip 150 (or at least through a portion of each) when the catheter is in an assembled state.

With reference to FIGS. 4 and 5, the elongate catheter body may comprise a first elongate member 120, a second elongate member 130, and a plurality of septal walls 140. The plurality of septal walls 140 may extend radially inward from the first elongate member 120 to the second elongate member 130 along a first length of the first elongate member 120. In some embodiments, the first length of the first elongate member 120 does not extend to the distal end of the first elongate member 120. Additionally or alternatively, the first length of the first elongate member 120 may or may not extend to the proximal end of the elongate catheter body 110. The plurality of septal walls 140, the first elongate member 120, and the second elongate member 130 may together define (in whole or in part) two or more lumens 162 disposed between the first elongate member 120 and the second elongate member 130.

In some embodiments, the plurality of septal walls may also extend radially inward from the first elongate member along a second length of the first elongate member without extending to (i.e., contacting) the second elongate member along the second length. The second length of the first elongate member may be disposed distal to the first length of the first elongate member. The portions of septal walls disposed along the second length of the first elongate member that do not extend to the second elongate member may be formed in the following manner: First, a distal portion of the catheter body comprising the second length of the first elongate member is formed by extrusion such that the septal walls extend from the first elongate member to the second elongate member along both the first and second lengths. Subsequently, portions of the septal walls disposed along the second length of the first elongate member are cut away or otherwise removed such that the septal walls do not extend from the first elongate member to the second elongate member along the second length. In some embodiments comprising septal walls that extend radially inward from the first elongate member along a second length of the first elongate member without extending to the second elongate member, disposing the catheter tip between the first elongate member and the second elongate member may cause the relative orientations of the catheter tip, first elongate member, and second elongate member to differ somewhat from that shown in FIG. 4. For example, a portion of the second length of the first elongate member may be forced radially away from the longitudinal axis of the elongate catheter body. Additionally or alternatively, the second elongate member and/or proximal portion of the catheter tip may be forced inward toward the longitudinal axis of the elongate catheter body. Furthermore, with the proximal end of the catheter tip disposed between the first elongate member and the second elongate member, prior to fusion of the catheter tip to the elongate catheter body, gaps may temporarily form between the first elongate member and the catheter tip due to interactions between the portions of the septal walls disposed along the second length of the first elongate member and the catheter tip.

As shown in FIG. 4, a proximal portion of the catheter tip 150 may be disposed between the first elongate member 120 and the second elongate member 130. With the proximal portion of the catheter tip 150 disposed between these components, the proximal portion of the catheter tip 150 may be fused to the elongate catheter body 110 via fusion to one or more of the second elongate member 130, the first elongate member 120, and the septal walls 140. Such fusion may be accomplished in various ways, for example (1) by applying heat to the elongate catheter body 110 and/or catheter tip (or portions thereof), and/or (2) through the use of one or more adhesives or other chemical fasteners (e.g., a solvent that softens or partially dissolves catheter components).

In some embodiments, fusion causes adjacent materials to blend. For example, upon fusion of one or more of the second elongate member 130, the first elongate member 120, and septal walls 140 to a portion of the catheter tip 150, material positioned adjacent the interface of these components may blend to some degree across a fusion interface (i.e., the post-fusion region (or regions) of a catheter that consist of blended material from both the catheter tip and one or more components of the elongate catheter body, for example the first elongate member, the second elongate member and/or the septal walls). In some embodiments, blending occurs across the entire thickness of a catheter tip 150 wall. In other embodiments, blending occurs only near the interface such that the catheter tip 150 comprises a layer that does not include material blended from the first elongate member or the second elongate member.

As shown in FIG. 5, which provides a cross-sectional view of the elongate catheter body 110 of the catheter 100 taken through line 5-5 of FIG. 4, the elongate catheter body 110 may comprise a first elongate member 120, a second elongate member 130, and septal walls 140. The second elongate member 130 may define, at least in part, a first lumen 160. The first elongate member 120, the second elongate member 130, and the septal walls 140 may define (in whole or in part) one or more radial lumens 162. The first lumen 160 may be centrally disposed such that the radial lumens 162 are peripherally disposed around the first lumen 160.

The first elongate member 120 may be generally cylindrical in shape and comprise a wall that is 0.003-0.010 inches thick. The second elongate member 130 may also be generally cylindrical in shape and comprise a wall that is 0.003-0.010 inches thick. In some embodiments, the wall of the second elongate member comprises a layer (e.g., a polyimide layer) with a thickness of 0.001-0.0035 inches.

The septal walls 140 may extend radially inward from the first elongate member 120 to the second elongate member 130. In this manner, the septal walls 140 may fixedly dispose at least a portion of the second elongate member 130 within the first elongate member 120. An elongate catheter body 110 may comprise any number of septal walls (e.g., 1, 2, 3, 4, or 5). Each septal wall may have a thickness of 0.003-0.007 inches and/or a height (i.e., the distance from the first elongate member to the second elongate member) of 0.005-0.017 inches.

In some embodiments, the first elongate member 120, the second elongate member 130, and the septal walls 140 (or portions of these components) are integrally formed via extrusion. For example, in some embodiments, an elastomer or other material is pushed or drawn through a die to form a portion of a catheter with a fixed cross-sectional profile. This portion of the catheter may comprise a portion of the first elongate member 120, a portion of the second elongate member 130, and a portion of the septal walls 140.

A first lumen 160 may be at least partially defined by the second elongate member 130. In some embodiments, the first lumen 160 comprises a diameter of 0.030-0.050 inches. This first lumen may be in fluid communication with a distal opening 156 and/or one or more ports 154 (see FIG. 1). Under some circumstances, when the catheter 100 is disposed within a body lumen, fluid may enter into the first lumen 160 through the distal opening 156 and/or one more ports 154. Such fluid may flow toward the proximal end of the catheter 100. By coupling the first lumen 160 to a pressure sensor, body fluid pressure (e.g., blood pressure) may be measured. Other sensors may be used to detect and/or measure other characteristics of the body fluid.

One or more radial lumens 162 may be defined, in whole or in part, by the septal walls 140, the first elongate member 120, and the second elongate member 130. In some embodiments, the one or more radial lumens 162 extend proximally from a fused region of the catheter 100 (i.e., the region over which the elongate catheter body 110 and the catheter tip 150 are fused together). Additionally or alternatively, in some embodiments (e.g., embodiments where the septal walls do not extend to the proximal end of the elongate catheter body 110), multiple radial lumens may combine adjacent the proximal end of the elongate catheter body 110. Under some circumstances, when a catheter 100 is disposed within a body lumen, body fluid within the body lumen may enter into the one or more radial lumens 162 via one or more side ports 122 (see FIG. 1). Such fluid may flow toward the proximal end of the catheter 100. By coupling the one or more radial lumens 162 to a pressure sensor, body fluid pressure (e.g., blood pressure), may be measured. Other sensors may be used to detect and/or measure other characteristics of the body fluid.

In some embodiments and circumstances, differences may be detected and/or measured between fluid that enters into a first lumen 160 and fluid that enters into one or more radial lumens 162 disposed between the first elongate member 120 and the second elongate member 130. For example, by coupling each lumen 160, 162 to a pressure sensor, the fluid pressures within each lumen may be measured and compared. Such a comparison may be useful in monitoring blood pressure across a valve (e.g., a heart valve during a valvuloplasty procedure).

For example, during an aortic valvuloplasty procedure, a catheter may be inserted into the radial or femoral artery of a patient and advanced within the patient's vasculature and heart such that a first lumen of the catheter is in primary fluid communication with blood on one side of the aortic valve (e.g., blood in the left ventricle) and a second lumen is in primary fluid communication with blood on the other side of the valve (e.g., blood in the aorta). More particularly, one or more distal openings (e.g., ports) of a catheter may be in primary fluid communication with a first lumen of a catheter and one or more proximal openings (e.g., ports) may be in primary fluid communication with a second lumen of a catheter. When the catheter is positioned in this manner, fluid from each side of the valve may enter into the corresponding lumen. By coupling each lumen to a pressure sensor, the practitioner may measure the fluid pressure inside the first lumen and the second lumen. From this data, the relative and/or absolute blood pressure on each side of the valve may be measured and compared.

Figure 6:
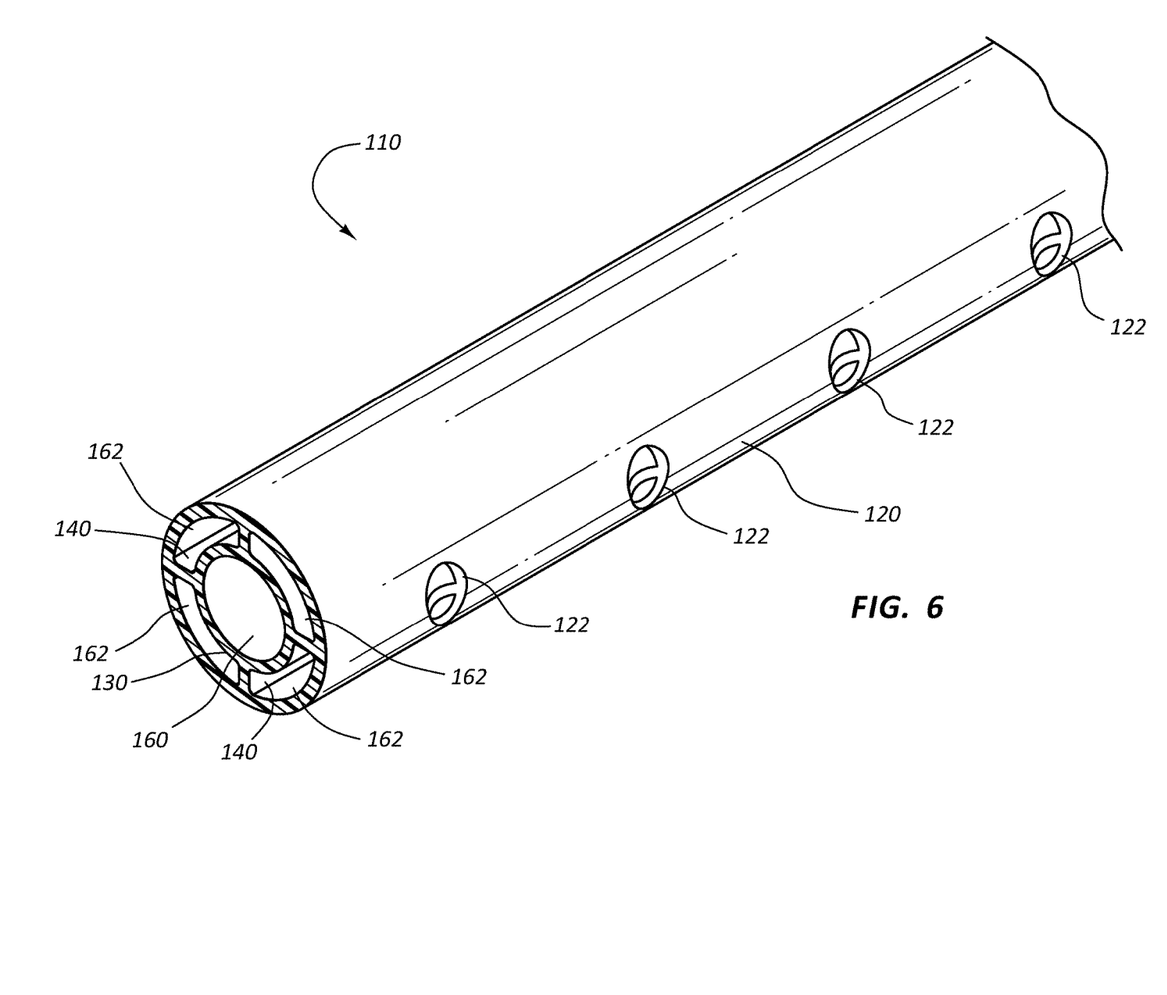
FIG. 6 is a perspective view of a portion of the assembled catheter of FIG. 1.

FIG. 6 provides a perspective view of a portion of the elongate catheter body 110. This figure shows the region of the elongate catheter body 110 that comprises ports 122, but omits portions of the elongate catheter body 110 that are disposed both proximal of and distal to this region. In the depicted embodiment, the elongate catheter body 110 comprises a first elongate member 120, a second elongate member 130, and septal walls 140. The first elongate member may comprise side ports 122. The side ports 122 may be configured to allow fluid from the external environment to enter into one or more radial lumens disposed between the first elongate member 120 and the second elongate member 130.

The side ports 122 may be arranged in any configuration along the length of the first elongate member 120. In some embodiments, such as that shown in FIG. 6, the ports 122 on one side of the first elongate member 120 are arranged along a line that is parallel to the longitudinal axis of the first elongate member 120, while ports 122 on the other side of the first elongate member 120 are arranged along a different line that is also parallel to the longitudinal axis of the first elongate member 120. The ports 122 on one side of the first elongate member 120 may be staggered with respect to the ports 122 on the other side of the first elongate member 120 (i.e., no port is disposed opposite another port) (see FIG. 1). In other embodiments, ports may be disposed opposite other ports.

In some catheters, each port provides direct access to only one lumen. For example, each port may be disposed between septal walls so as to provide direct access only to one radial lumen. In other embodiments, such as that shown in FIG. 6, the ports 122 extend through both the first elongate member 120 and through at least a portion of the septal walls 140. With the ports 122 disposed in this manner, fluid from the external environment may pass through the ports 122 into either a first radial lumen or a second radial lumen.

The side ports 122 may be introduced into the elongate catheter body 110 by any of various methods. For example, in some embodiments, one or more ports 122 may be skived into the first elongate member 120 and/or a septal wall 140. Additionally or alternatively, the ports 122 may be introduced by boring a hole through the first elongate member 120 to access one or more radial lumens 162.

In some embodiments, such as those depicted in FIGS. 1-6, the only lumen that extends through the catheter tip 150 is a central lumen 160. In other embodiments, one or more additional lumens extend through the catheter tip.

Figure 7:
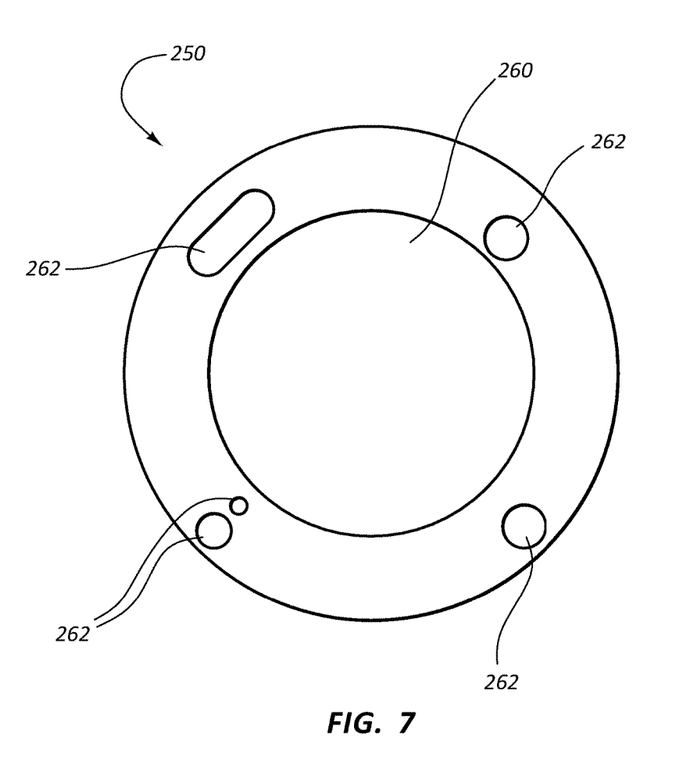
FIG. 7 is an end view of a catheter tip.

For example, FIG. 7 provides an end view of a catheter tip 250 through which more than one lumen extends. The catheter tip 250 may resemble the catheter tip 150 described above in certain respects. Relevant disclosure set forth above regarding similar features thus may not be repeated hereafter. Moreover, specific features of the catheter 100 and components thereof shown in FIGS. 1-6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter tip and related components of FIG. 7. Any suitable combination of the features, and variations of the same, described with respect to the catheter and related components illustrated in FIGS. 1-6, can be employed with the catheter tip of FIG. 7 and vice versa. This pattern of disclosure applies equally to further embodiments depicted in subsequent figures and described hereafter.

As noted above, FIG. 7 provides an end view of a catheter tip 250 through which more than one lumen extends. In particular, in the illustrated embodiment, both a central lumen 260 and one or more radial lumens 262 extend through the catheter tip 250. In some embodiments, the one or more radial lumens 262 are disposed within the walls of a catheter tip 250. In other words, a radial lumen 262 of a catheter tip 250 may be defined by an interior surface of a cavity disposed within the wall of the catheter tip 250.

The catheter tip 250 may be coupled to an elongate catheter body, such as the elongate catheter body 110 described above in connection with FIGS. 1-6. For example, the catheter tip may be coupled to the elongate catheter body 110 such that lumen 260 (i.e., a hollow region disposed between the inner walls of the catheter tip 250) is in fluid communication with the central lumen in the elongate catheter body 110 (identified as at least part of lumen 160 in FIGS. 1-6). Similarly, when the catheter tip 250 is coupled to the elongate catheter body 110, the one or more radial lumens 262 of the catheter tip 250 may be in fluid communication with one or more radial lumens 160 of the elongate catheter body 110. In some embodiments each radial lumen 262 is in direct fluid communication with only one radial lumen 162 of the elongate catheter body 110. In other embodiments, two or more radial lumens 262 may be in direct fluid communication with a single radial lumen 162 of the elongate catheter body 110. In other words, multiple radial lumens 262 within the distal tip 250 may be in direct fluid communication with the same lumen 162 of the elongate catheter body 110. Further, in some embodiments, the cross-sectional profile of a radial lumen 262 of the catheter tip 250 may have the same general shape as the cross-sectional profile of the radial lumen 162 of the elongate catheter body 110.

Together, the one or more radial lumens 162 of the elongate catheter body 110 and the one or more radial lumens 262 of the catheter tip 250 may provide a separate path (distinct from the path defined by the combined central lumen 160, 260) that extends from the proximal end of the catheter 200 to the distal end of the catheter tip 250. In some circumstances, fluid may be introduced or removed from a patient via a combined radial lumen (i.e., a lumen comprising a radial lumen 162 of the elongate catheter body 110 and a radial lumen 262 of the catheter tip 250). In some circumstances, an elongate medical appliance may be inserted and/or withdrawn through such a combined lumen. For example, a first wire may be threaded through both a radial lumen 162 of the elongate catheter body 110 and a radial lumen 262 of the catheter tip 250 and be positioned adjacent the distal end of the catheter tip 250. A second wire may be threaded through a combined central lumen 160, 260, or through another combined radial lumen 162, 262. In some circumstances, an electrode may be disposed adjacent the distal end of the wire. When the wires and electrodes are disposed in this manner, a practitioner may use the wire(s) and electrode(s) to monitor and/or deliver an electrical pulse. In other or further circumstances, one or more sensors may be deployed through one or more radial lumens 162, 262. Further, in some embodiments, a wire disposed within a one or more combined radial lumens 162, 262 may not be displaceable during therapy.

In some embodiments, a wire or other elongate member comprising a shape-memory material (e.g., a superelastic alloy) may be disposed within a radial lumen 262 of the catheter tip 250. For example, in some embodiments, a wire comprising Nitinol may be disposed within one or more radial lumens 262. The shape-memory material may exert a force on the catheter tip 250, causing the catheter tip 250 to adopt a conformation that differs from the conformation that the catheter tip 250 would adopt in the absence of the shape-memory material. For example, insertion of a shape-memory material into a catheter tip 250 may cause the catheter tip 250 to bend from its natural state. Additionally or alternatively, in some embodiments, a wire (e.g., a shape-memory wire) disposed within a radial lumen 262 of a catheter tip 250 may alter one or more characteristics of the catheter tip 250. For example, the wire may increase the hardness and/or rigidity of the catheter tip 250. In other or further embodiments, the wire may improve the pushability and/or torqueability of the catheter tip 250. For example, the wire may increase the torque transference per unit length across the catheter tip 250 and/or improve the longitudinal transfer of force across the catheter tip 250 relative to comparable embodiments that lack the a wire disposed within a radial lumen 262.

A catheter tip 250 that comprises more than one lumen may be fused to an elongate catheter body 110 by any suitable method. For example, the catheter tip 250 may be fused to an elongate catheter body 110 via a method similar to the methods described below in connection with FIGS. 8A-8D.

Alternatively or additionally, prior to fusion of the catheter tip 250 to the elongate catheter body 110, a wire or mandrel may be inserted through a portion of the one or more radial lumens 262 and disposed adjacent the fusion region. With the wire or mandrel disposed within the one or more radial lumens 262 in this manner, the catheter tip 250 may be fused with the elongate catheter body 110. Subsequent to fusion, the wire or mandrel may be withdrawn from the one or more radial lumens 262. Manipulating the wire or mandrel in this manner may preserve the integrity of the one or more radial lumens 262 during the fusion process (e.g., prevent collapse of the lumen during fusion). Further, the shape of the wire disposed within a radial lumen 262 may at least partially define the shape of the portion of the radial lumen 262 disposed adjacent the fusion region.

FIGS. 8A-8D are schematic depictions of a catheter 300 (or components thereof). More particularly, FIGS. 8A-8D depict a catheter 300 (or components thereof) in various states, with each state corresponding to a state of the catheter (or catheter components) during an exemplary method of its manufacture. Analogous methods may or may not proceed through each step depicted in FIGS. 8A-8D. Additionally, analogous methods may include steps not shown in these figures. Procedures with any sub-combination of the steps recited below are also within the scope of this disclosure.

Figures 8A, 8B, 8C:
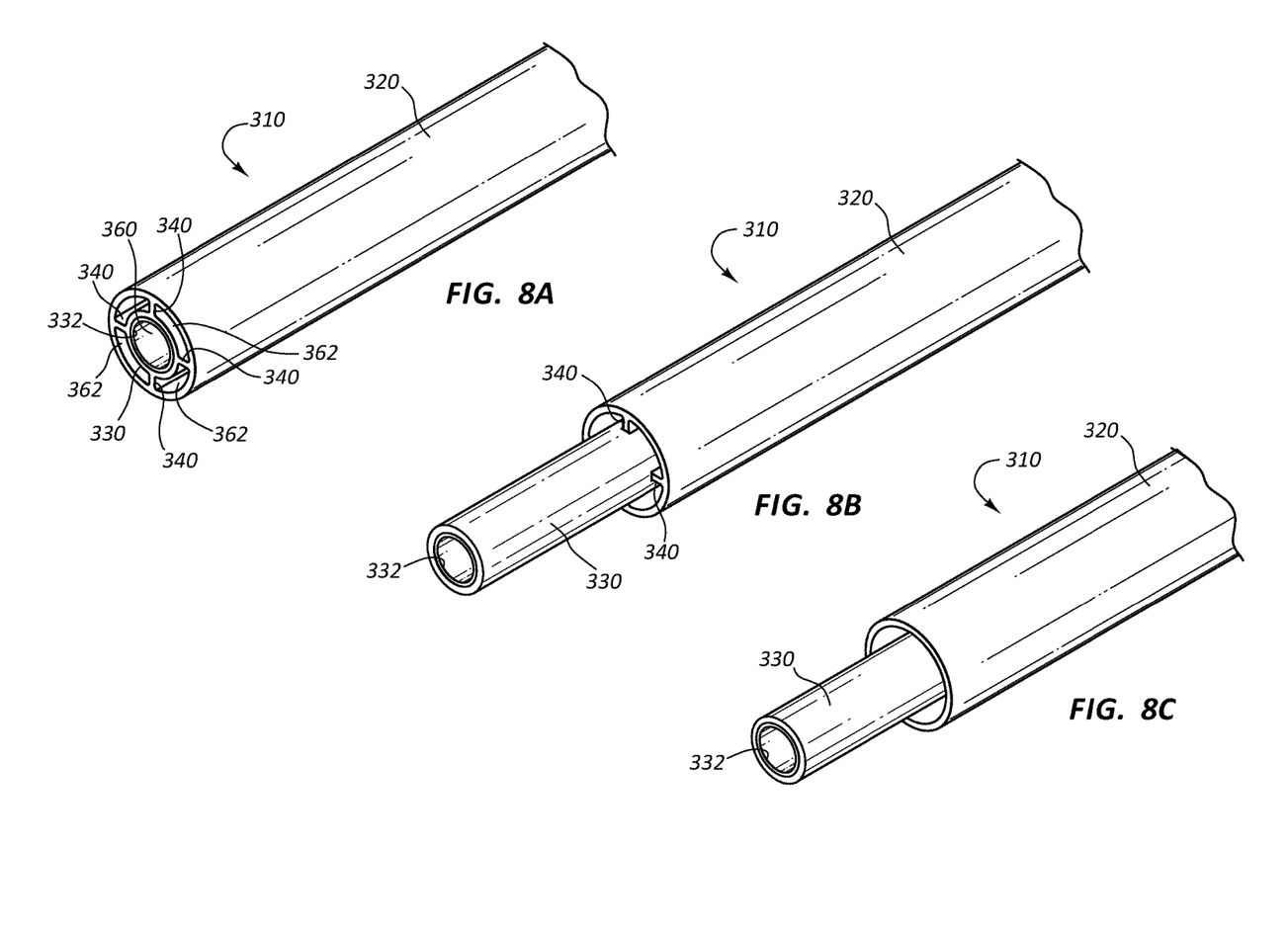
FIG. 8A is a perspective view of a distal portion of an elongate catheter body in a first state.
FIG. 8B is a perspective view of the distal portion of the elongate catheter body of FIG. 8A in a second state.
FIG. 8C is a perspective view of the distal portion of the elongate catheter body of FIG. 8A in a third state.

FIG. 8A provides a perspective view of a distal portion of an elongate catheter body 310 in a first state. As depicted in FIG. 8A, the elongate catheter body 310 has a fixed cross-sectional profile that extends along a distal-most portion of the elongate catheter body 310. The elongate catheter body 310, as depicted in this figure, may be produced by extruding material, such as material comprising a thermoplastic elastomer, through a die. The extruded product may comprise a first elongate member 320, a second elongate member 330, and septal walls 340. In some embodiments, the second elongate member 330 comprises a liner 332 (e.g., a polyimide liner). The liner 332 may define the interior diameter of the second elongate member 330. Additionally or alternatively, the liner 332 may increase the hardness, stiffness, pressure capacity, and/or durability of the second elongate member 330. In some embodiments, the liner 332 may be applied to a thermoplastic layer after the thermoplastic portion of the elongate catheter body 310 has been extruded.

FIG. 8B provides a perspective view of a distal portion of the elongate catheter body 310 in a second state that differs somewhat from the first state shown in FIG. 8A. In particular, compared to the extruded material shown in FIG. 8A, the elongate catheter body 310 depicted in FIG. 8B lacks the distal-most portions of the first elongate member 320 and the distal-most portions of the septal walls 340. Thus, the distal portion of the second elongate member 330 extends beyond a distal end of the first elongate member 320. The embodiment shown in FIG. 8B may be produced from the embodiment shown in FIG. 8A by cutting away or otherwise removing distal portions of the first elongate member 320 and distal portions of the second elongate member 330.

FIG. 8C provides a perspective view of a distal portion of the elongate catheter body 310 in a third state that differs somewhat from the second state shown in FIG. 8B. In particular, the septal walls of the elongate catheter body 310 shown in FIG. 8B do not extend both longitudinally to the distal end of the first elongate member 320 and radially inward from the first elongate member 320 to the second elongate member 330. To manufacture an elongate catheter body 310 in this third state from the elongate catheter body in the second state shown in FIG. 8B, the septal walls may be cut or otherwise removed along a second (e.g., distal-most) length of the first elongate member such that the septal walls do not extend from the first elongate member to the second elongate member along the second length. In the illustrated embodiment, the septal walls 340 have been completely removed along the second length of the first elongate member 320. In other embodiments, portions of the septal walls 340 may remain along the second length of the first elongate member 320, yet not extend from the first elongate member 320 to the second elongate member 330. Similarly, an analogous method may be used to cut away or remove the septal walls along a distal-most length of the first elongate member in embodiments where the elongate catheter body does not comprise a second elongate member with a distal portion that extends beyond the distal end of the first elongate member.

Figure 8D:
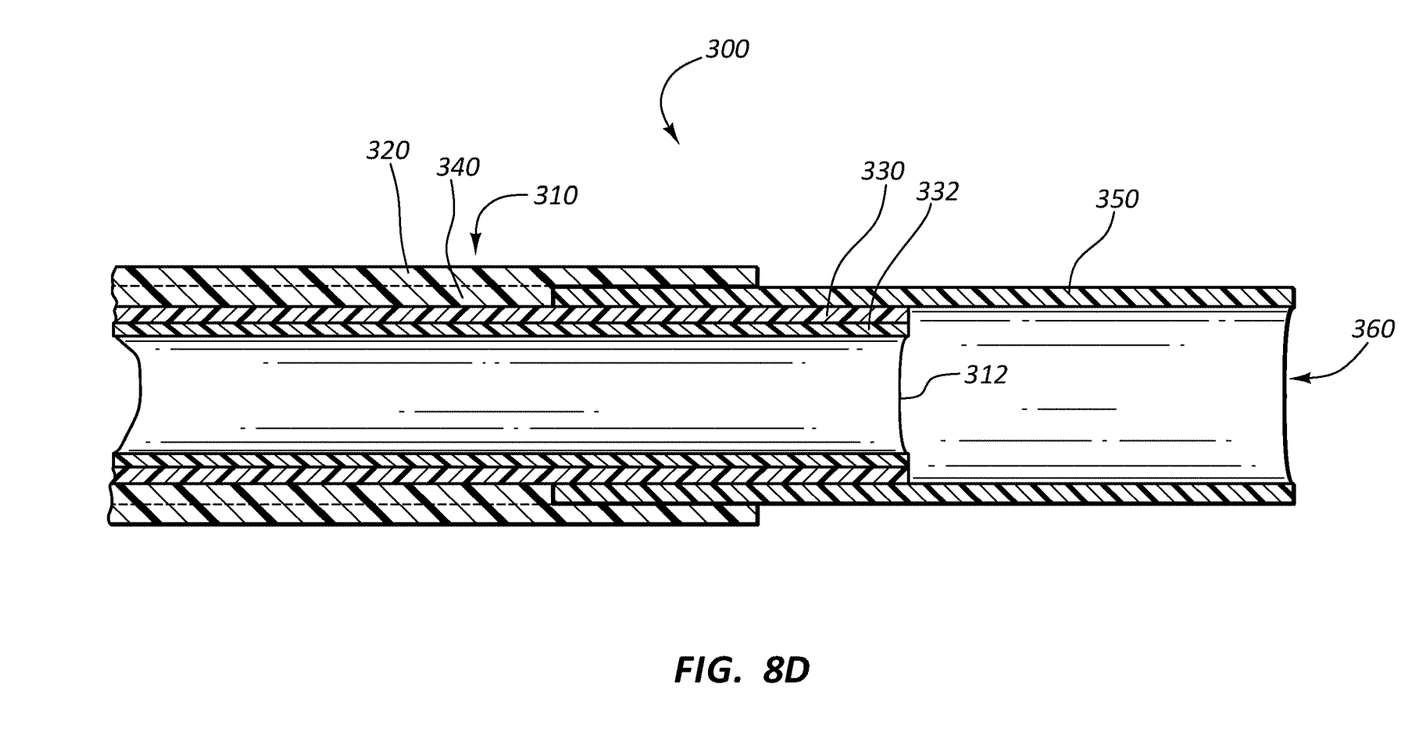
FIG. 8D is a cross-sectional side view of the distal portion of the elongate catheter body of FIG. 8C coupled to an elongate catheter tip.

FIG. 8D provides a cross-sectional side view of a catheter 300 that comprises an elongate catheter body 310 coupled to an elongate catheter tip 350. To couple the elongate catheter body 310 shown in FIG. 8C to an elongate catheter tip 350, the distal tip 350 may be inserted into the elongate catheter tip 310 such that a proximal portion of the catheter tip 350 is disposed between a first elongate member 320 and a second elongate member 330. For example, the elongate catheter tip 350 may be disposed around a portion of the second elongate member 330 and disposed within a distal portion of the first elongate member 320. In other words, the elongate catheter body 310 may be disposed on both an inner diameter and an outer diameter of the tubular distal portion. With the proximal portion of the catheter tip 350 disposed between the first elongate member 320 and the second elongate member 330, the proximal portion of the catheter tip 350 may be fused to the elongate catheter body 310 via fusion to one or more of the second elongate member 330, the first elongate member 320, and the septal walls 340.

Figure 9:
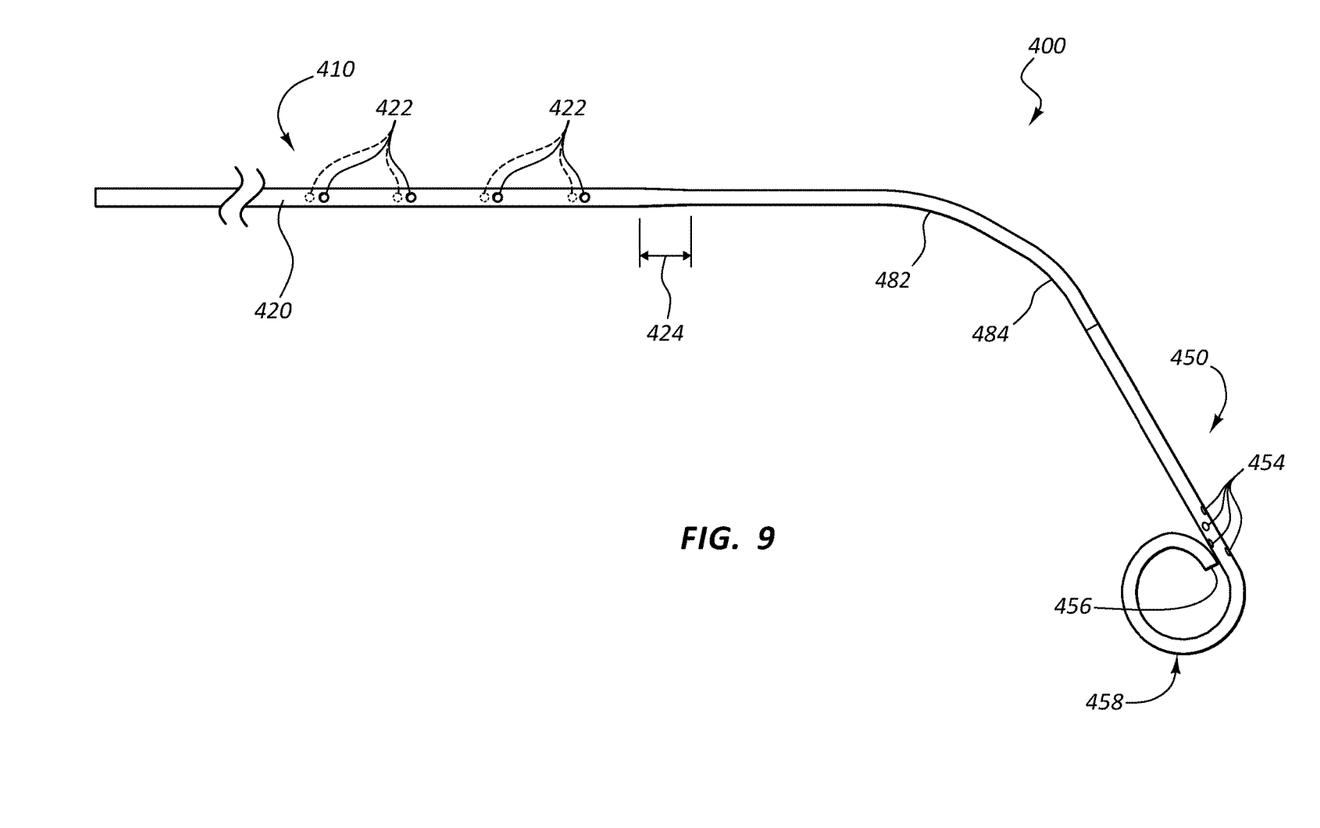
FIG. 9 depicts a side view of a catheter in an assembled state.

FIG. 9 provides a side view of a catheter 400 in an assembled state. The catheter 400 comprises an elongate catheter body 410 and an elongate catheter tip 450. The embodiment depicted in FIG. 9 comprises a first elongate member 420, side ports 422, a tapered region 424, side ports 454, distal opening 456, and a curved distal region 458 analogous to similar elements disclosed above in connection with previously described figures. As shown in the illustrated embodiment, the catheter 400 may comprise one or more bends, such as bends 482 and 484 of the elongate catheter body 410, each of which connect generally straight portions of the catheter 400 (as used herein, generally straight portions of the catheter are portions that are either straight or have a radius of curvature that is greater than the radius of curvature of an adjacent bend (e.g., bend 482 or 484)). In some embodiments, the bends 482, 484 connect generally straight portions of the catheter that are disposed at an interior angle relative to one another of between 95 degrees and 175 degrees, between 105 degrees and 165 degrees, or between 120 degrees and 150 degrees. The one or more bends 482, 484 in the catheter 400 may assist a practitioner in guiding the catheter 400 to a desired location within a patient. For example, a catheter 400 with two bends (e.g., a catheter with a first bend 482 and a second bend 484 that is disposed distal of the first bend 482) may be configured to facilitate insertion and/or guidance of a catheter 400 that enters a patient via a radial insertion point. A catheter comprising only one bend, such as the embodiment depicted in FIG. 1, may be configured to facilitate insertion and/or guidance of a catheter that enters a patient via a femoral insertion point.

One of ordinary skill in the art, having the benefit of this disclosure, will recognize that the position and/or structure of the bends may be altered for any number of purposes. For example, the distance between bends, the angle(s) traversed by one or more of the bends, and the number of bends may be altered based on the intended use of the catheter, the anatomy of the patient, etc. Similarly, the length of the catheter tip 150 may be altered to facilitate insertion and/or guidance of the catheter to the proper location within a patient.

In some embodiments, the elastomeric material of the catheter 400 may be predisposed to adopt a curved configuration, thereby forming (or contributing to) a bend 482, 484 in the catheter 400. Additionally or alternatively, a shape-memory material, such as Nitinol, may be disposed within the elongate catheter body 410 and/or the elongate catheter tip 450, thereby forming (or contributing to) a bend 482, 484 in the catheter 400. For example, in some embodiments, a Nitinol wire may be disposed within one or more radial lumens of the elongate catheter body 410. The Nitinol may thus exert a force on the elongate catheter body 410, causing the elongate catheter body 410 to adopt a curved conformation that differs from the conformation that the elongate catheter body 410 would adopt in the absence of the shape-memory material. Insertion of such a wire may also increase the hardness or rigidity of the elongate catheter body 410. In other or further embodiments, the wire may improve the pushability and/or torqueability of the elongate catheter body 410. For example, the wire may increase the torque transference per unit length across the elongate catheter body 410 and/or improve the longitudinal transfer of force across the elongate catheter body 410 relative to comparable embodiments that lack the a wire disposed within the elongate catheter body 410.

In some embodiments, the shape-memory material may be inserted and/or sealed within a radial lumen of a catheter during the manufacturing process. In other embodiments, the shape-memory material may be inserted in a radial lumen by a practitioner. In this manner, the practitioner may introduce various bends at various locations of the catheter by inserting different shape-memory wires into the catheter.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, only a portion of a method described herein may be a separate method. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of this disclosure.

The invention claimed is:

1. A catheter comprising:
   an elongate catheter body, comprising:
   a distal end;
   a first elongate member; and
   a second elongate member that is at least partially disposed within the first elongate member;

an elongate catheter tip coupled to the first elongate member and the second elongate member adjacent the distal end of the elongate catheter body, the elongate catheter tip comprising a proximal portion disposed between the first elongate member and the second elongate member such that the proximal portion of the catheter tip is both disposed around a portion of the second elongate member and disposed within a distal portion of the first elongate member;

a first lumen extending through both the second elongate member and the elongate catheter tip;

a second lumen comprising a first portion, the first portion of the second lumen disposed proximal of the catheter tip and between the first elongate member and the second elongate member; and a third lumen disposed within the catheter tip and in communication with the second lumen, wherein the first lumen is centrally disposed and the second lumen and the third lumen are peripherally disposed around the first lumen.

2. The catheter of claim 1, wherein
the elongate catheter body comprises a first set of material properties and the catheter tip comprises a second set of material properties, and
the first set of material properties differs from the second set of material properties.

3. The catheter of claim 2, wherein the elongate catheter body has a durometer hardness which is greater than the durometer hardness of the catheter tip.

4. The catheter of claim 1, wherein the proximal portion of the catheter tip is fused to the first elongate member and the second elongate member such that:
material from the proximal portion of the catheter tip, the first elongate member, and the second elongate member blend across a fusion interface; and
the proximal portion of the catheter tip comprises a layer that does not include blended material from the first elongate member or the second elongate member.

5. The catheter of claim 1, wherein the elongate catheter body further comprises:
a plurality of septal walls extending radially inward from the first elongate member to the second elongate member along a first length of the first elongate member, the first length of the first elongate member disposed proximal of a second length of the first elongate member; and
a plurality of radial lumens, one of which is the second lumen, wherein the plurality of radial lumens is defined, at least in part, by the plurality of septal walls, the first elongate member, and the second elongate member;
and the plurality of radial lumens is disposed proximal of the catheter tip, radially from a longitudinal axis of the first lumen, and between the first elongate member and the second elongate member.

6. The catheter of claim 1, wherein
the elongate catheter tip comprises one or more openings configured to allow fluid to enter into the first lumen; and
the first elongate member comprises one or more side ports configured to allow fluid to enter into the second lumen.

7. The catheter of claim 1, wherein the second elongate member comprises a distal portion that extends beyond a distal end of the first elongate member.

8. The catheter of claim 1, wherein a distal end of the second elongate member and a distal end of the first elongate member are flush with one another.

9. The catheter of claim 1, wherein a distal end of the second elongate member is disposed proximal of a distal end of the first elongate member.

10. The catheter of claim 1, wherein at least portions of the first elongate member, the second elongate member, and the septal walls are integrally formed.

11. The catheter of claim 1, wherein, the elongate catheter body or the elongate catheter tip comprises a first bend that connects generally straight portions of the catheter, the generally straight portions disposed at an interior angle relative to one another of between 95 degrees and 175 degrees.

12. The catheter of claim 11, wherein the catheter comprises a second bend that connects generally straight portions of the catheter, the generally straight portions disposed at an interior angle relative to one another of between 95 degrees and 175 degrees.

13. A method of forming a catheter by coupling a catheter tip to a catheter body, the method comprising:
obtaining an elongate catheter body, comprising:
a distal end;
a first elongate member; and
a second elongate member that is at least partially disposed within the first elongate member;
obtaining an elongate catheter tip comprising a proximal portion;
disposing the proximal portion of the catheter tip between the first elongate member and the second elongate member such that the proximal portion of the catheter tip is both disposed around a portion of the second elongate member and disposed within a distal portion of the first elongate member; and
coupling the proximal portion of the elongate catheter tip to both the first elongate member and the second elongate member adjacent to the distal end of the elongate catheter body;
wherein, subsequent to coupling of the proximal portion of the catheter tip to both the first elongate member and the second elongate member, the catheter comprises a first lumen extending through both the second elongate member and the elongate catheter tip, a second lumen comprising a first portion disposed proximal of the catheter tip and between the first elongate member and the second elongate member, and a third lumen disposed within the catheter tip and in communication with the second lumen; and
wherein the first lumen is centrally disposed and the second lumen and the third lumen are peripherally disposed around the first lumen.

14. The method of claim 13, further comprising coupling a distal portion of the second elongate member to the elongate catheter tip, the distal portion of the second elongate member extending beyond a distal end of the first elongate member.

15. The method of claim 13, wherein coupling the proximal portion of the catheter tip to both the first elongate member and the second elongate member comprises applying heat to the elongate catheter body and the elongate catheter tip.

16. The method of claim 13, wherein coupling the proximal portion of the catheter tip to both the first elongate member and the second elongate member comprises the use of an adhesive and/or solvent.

17. The method of claim 13, wherein coupling the proximal portion of the catheter tip to both the first elongate member and the second elongate member comprises forming a tapered region, the tapered region comprising a portion of the first elongate member, a portion of the catheter tip, a distal end, and a proximal end, wherein the distal end of the tapered region has a smaller outer diameter than the proximal end of the tapered region.

18. The method of claim 13, further comprising disposing a mandrel within a radial lumen of the catheter tip prior to coupling the proximal portion of the catheter tip to both the first elongate member and the second elongate member.

* * * * *